United States Patent
Manzella et al.

(10) Patent No.: US 9,707,570 B2
(45) Date of Patent: *Jul. 18, 2017

(54) BEARING FOR UMBILICUS OF A FLUID PROCESSING SYSTEM

(71) Applicant: Fenwal, Inc., Lake Zurich, IL (US)

(72) Inventors: Salvatore Manzella, Barrington, IL (US); Gregory G. Pieper, Spring Grove, IL (US)

(*) Notice: Subject to any disclaimer, the term of this patent is extended or adjusted under 35 U.S.C. 154(b) by 0 days.

This patent is subject to a terminal disclaimer.

(21) Appl. No.: 15/376,612

(22) Filed: Dec. 12, 2016

(65) Prior Publication Data

US 2017/0100726 A1    Apr. 13, 2017

Related U.S. Application Data

(63) Continuation of application No. 14/693,518, filed on Apr. 22, 2015, now Pat. No. 9,545,637.

(51) Int. Cl.
*B04B 9/12* (2006.01)
*B04B 5/04* (2006.01)
(Continued)

(52) U.S. Cl.
CPC ............. *B04B 9/12* (2013.01); *A61M 1/3693* (2013.01); *B04B 5/0442* (2013.01); *F16C 17/12* (2013.01);
(Continued)

(58) Field of Classification Search
CPC . B04B 9/12; B04B 2005/0492; B04B 5/0442; A61M 1/3693; F16C 17/12; F16C 2316/10
(Continued)

(56) References Cited

U.S. PATENT DOCUMENTS 2,832,374 A * 4/1958 November ............ F16L 11/22
  138/111
2,936,791 A * 5/1960 Farrar ................. F16L 11/22
  138/111
(Continued)

FOREIGN PATENT DOCUMENTS

EP      2397228 A2 * 12/2011  .......... B04B 5/0442
JP    01164888 A *  6/1989
(Continued)

OTHER PUBLICATIONS

European Patent Office, Extended European Search Report for EP3085451A1, dated Sep. 28, 2018.

*Primary Examiner* — Charles Cooley
(74) *Attorney, Agent, or Firm* — Hanna Yoon; Scott M. Day

(57) ABSTRACT

A fluid circuit for use with a fluid processing assembly, the fluid circuit comprising an umbilicus having a first end, a second end, an axis of rotation, and a cross-sectional circumference; a one-piece bearing secured to the umbilicus at a location between the first and second ends, the bearing having an axis of rotation and including an inner lumen which directly engages the umbilicus and includes a plurality of traction features, which bear against the umbilicus to prevent relative rotation of the bearing and the umbilicus; and the plurality of traction features comprising a first traction feature configured to engage the umbilicus at a first set of lengths between the first and second ends and a second traction feature configured to engage the umbilicus at a second set of lengths between the first and second ends.

18 Claims, 12 Drawing Sheets

(51) Int. Cl.
*A61M 1/36* (2006.01)
*F16C 17/12* (2006.01)

(52) U.S. Cl.
CPC ... B04B 2005/0492 (2013.01); F16C 2316/10 (2013.01)

(58) Field of Classification Search
USPC ............ 494/17–18, 21, 45, 83–84; 138/111; 210/380.1, 380.3, 781, 782
See application file for complete search history.

(56) References Cited

U.S. PATENT DOCUMENTS

| | | | | |
|---|---|---|---|---|
| 3,747,632 | A * | 7/1973 | Kok | B29C 44/18 137/375 |
| 4,018,304 | A * | 4/1977 | Lolachi | B04B 5/0442 184/6 |
| 4,056,224 | A * | 11/1977 | Lolachi | A61M 1/3693 494/18 |
| 4,108,353 | A * | 8/1978 | Brown | B04B 9/08 494/18 |
| 4,109,852 | A * | 8/1978 | Brown | B04B 5/0442 494/18 |
| 4,109,854 | A * | 8/1978 | Brown | B04B 5/0442 494/18 |
| 4,109,855 | A * | 8/1978 | Brown | B04B 9/08 494/18 |
| 4,114,802 | A * | 9/1978 | Brown | B04B 5/0442 174/86 |
| 4,120,449 | A * | 10/1978 | Brown | B04B 5/00 494/18 |
| 4,163,519 | A * | 8/1979 | Stabile | B04B 5/0442 494/18 |
| 4,164,318 | A * | 8/1979 | Boggs | B04B 5/0442 494/18 |
| 4,194,684 | A * | 3/1980 | Boggs | B04B 5/0442 494/18 |
| 4,221,322 | A * | 9/1980 | Drago | B04B 5/0442 494/18 |
| 4,245,383 | A * | 1/1981 | Boggs | B04B 5/0442 264/164 |
| 4,261,507 | A * | 4/1981 | Baumler | B04B 5/0442 494/45 |
| 4,372,484 | A * | 2/1983 | Larsson | B04B 5/0442 422/561 |
| 4,385,021 | A * | 5/1983 | Neeley | H01B 7/0072 138/111 |
| 4,389,206 | A * | 6/1983 | Bacehowski | B04B 5/0442 494/42 |
| 4,389,207 | A * | 6/1983 | Bacehowski | B04B 5/0442 138/111 |
| 4,425,112 | A * | 1/1984 | Ito | B04B 5/00 494/18 |
| 4,439,178 | A * | 3/1984 | Mulzet | B04B 5/0442 494/18 |
| 4,459,169 | A * | 7/1984 | Bacehowski | B04B 5/0442 138/111 |
| 4,636,193 | A * | 1/1987 | Cullis | A61M 1/3693 215/12.1 |
| 4,710,161 | A * | 12/1987 | Takabayashi | B04B 5/0442 494/10 |
| 4,778,444 | A * | 10/1988 | Westberg | B04B 5/0442 494/18 |
| 4,865,081 | A * | 9/1989 | Neumann | B04B 5/0442 138/103 |
| 4,950,401 | A * | 8/1990 | Unger | B04B 5/0442 210/360.1 |
| 5,160,310 | A * | 11/1992 | Yhland | B04B 5/0428 210/360.1 |
| 5,360,542 | A * | 11/1994 | Williamson, IV | A61M 1/308 210/232 |
| 5,362,291 | A * | 11/1994 | Williamson, IV | B04B 5/0428 494/12 |
| 5,449,022 | A * | 9/1995 | Witthaus | B04B 5/0442 138/103 |
| 5,501,840 | A * | 3/1996 | Mantovani | A61M 39/08 138/111 |
| 5,514,069 | A * | 5/1996 | Brown | B04B 5/0442 138/103 |
| 5,551,942 | A * | 9/1996 | Brown | B04B 5/0442 494/18 |
| 5,704,887 | A * | 1/1998 | Slowik | B04B 5/0442 210/232 |
| 5,772,159 | A * | 6/1998 | Wendt | F16C 1/262 248/27.1 |
| 5,989,177 | A * | 11/1999 | West | B04B 5/0442 464/106 |
| 5,996,634 | A * | 12/1999 | Dennehey | B04B 5/0442 138/109 |
| 6,267,537 | B1 * | 7/2001 | Breivik | E21B 17/015 166/350 |
| 6,344,020 | B1 * | 2/2002 | Reitz | B04B 5/0442 384/523 |
| 6,419,073 | B1 * | 7/2002 | Piron | B65G 17/005 198/370.02 |
| 6,800,054 | B2 * | 10/2004 | Westberg | A61M 1/38 494/43 |
| 6,832,981 | B2 * | 12/2004 | Witthaus | B04B 5/0442 138/111 |
| 6,979,776 | B1 * | 12/2005 | Zimmermann | H02G 1/06 138/111 |
| 7,001,321 | B1 * | 2/2006 | Brown | B04B 5/0428 494/18 |
| 7,008,366 | B1 * | 3/2006 | Aitkenhead | B04B 5/0442 138/111 |
| 7,452,323 | B2 * | 11/2008 | Aitkenhead | B04B 5/0442 494/45 |
| 7,849,885 | B2 * | 12/2010 | Olsen | F16L 11/081 138/109 |
| 8,216,120 | B2 * | 7/2012 | Aitkenhead | B04B 5/0442 494/45 |
| 8,257,239 | B2 * | 9/2012 | Manzella, Jr. | B04B 5/0442 138/111 |
| 8,277,369 | B2 * | 10/2012 | West | B04B 5/0442 384/300 |
| 8,460,165 | B2 * | 6/2013 | Manzella, Jr. | B04B 5/0442 138/111 |
| 8,657,730 | B2 * | 2/2014 | Manzella | B04B 5/0442 138/111 |
| 9,101,944 | B2 * | 8/2015 | Manzella | B04B 5/0442 |
| 9,383,044 | B2 * | 7/2016 | Chung | B29D 22/00 |
| 9,545,637 | B2 * | 1/2017 | Manzella | A61M 1/3693 |
| 2002/0195154 | A1* | 12/2002 | Witthaus | B04B 5/0442 138/111 |
| 2006/0111229 | A1* | 5/2006 | Aitkenhead | B04B 5/0442 494/83 |
| 2009/0239730 | A1* | 9/2009 | Aitkenhead | B04B 5/0442 494/18 |
| 2011/0303316 | A1* | 12/2011 | Manzella, Jr. | B04B 5/0442 138/106 |
| 2011/0306913 | A1* | 12/2011 | West | B04B 5/0442 604/5.01 |
| 2012/0312408 | A1* | 12/2012 | Manzella, Jr. | B04B 5/0442 138/106 |
| 2013/0248040 | A1* | 9/2013 | Manzella | B04B 5/0442 138/106 |
| 2013/0304039 | A1* | 11/2013 | Chung | A61M 39/105 604/537 |
| 2014/0230944 | A1* | 8/2014 | Chung | B29D 22/00 138/109 |
| 2014/0274648 | A1* | 9/2014 | Pieper | B04B 5/0442 494/18 |

(56) References Cited

U.S. PATENT DOCUMENTS

2016/0310968 A1* 10/2016 Manzella ............ A61M 1/3693
2017/0100726 A1*  4/2017 Manzella .................. B04B 9/12

FOREIGN PATENT DOCUMENTS

| WO | WO 9517261 A1 * | 6/1995 | ........... B04B 5/0442 |
| WO | WO 9846363 A1 * | 10/1998 | ........... B04B 5/0442 |
| WO | WO 2004046601 A1 * | 6/2004 | ............ F16L 11/081 |

* cited by examiner

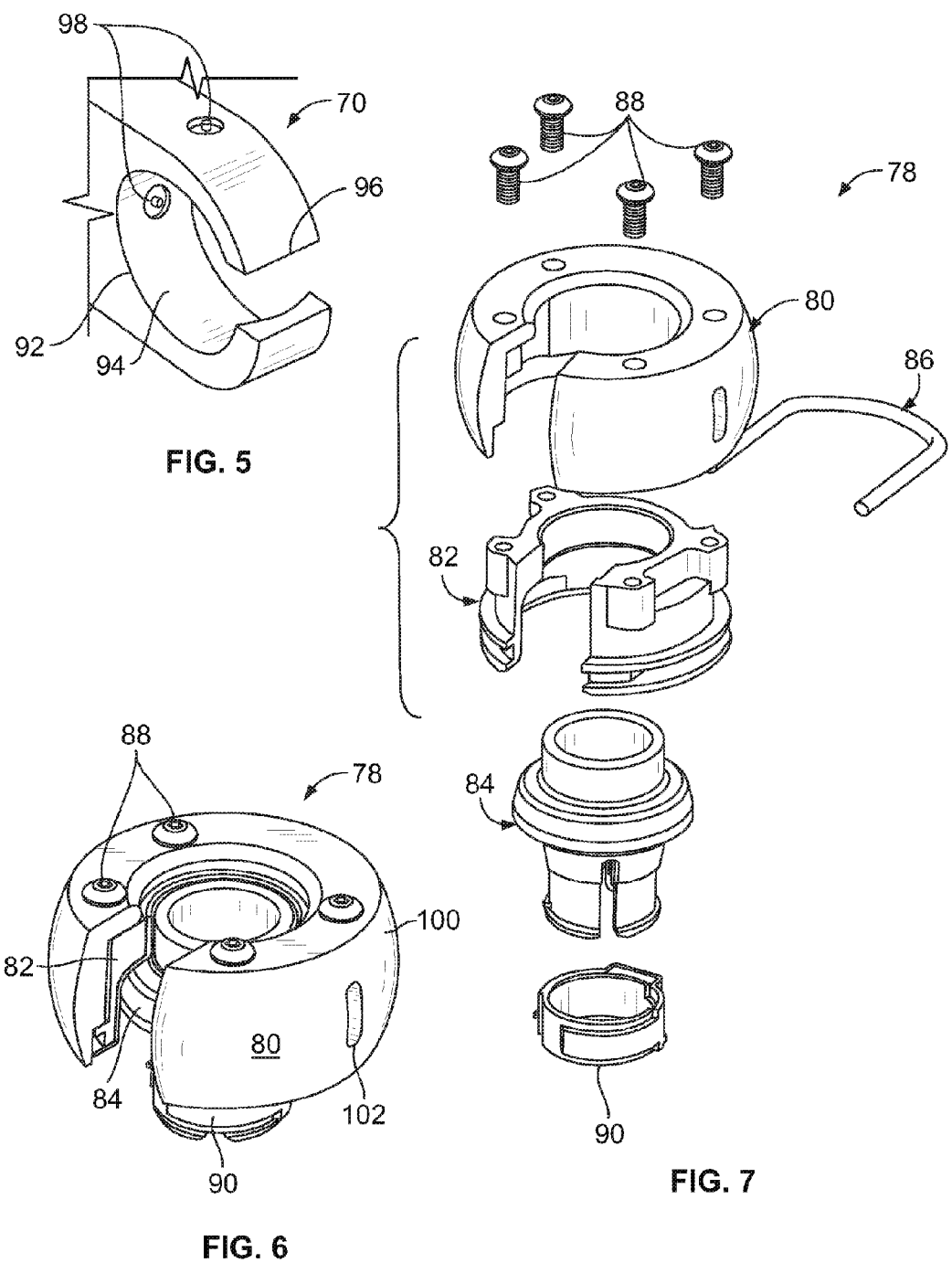

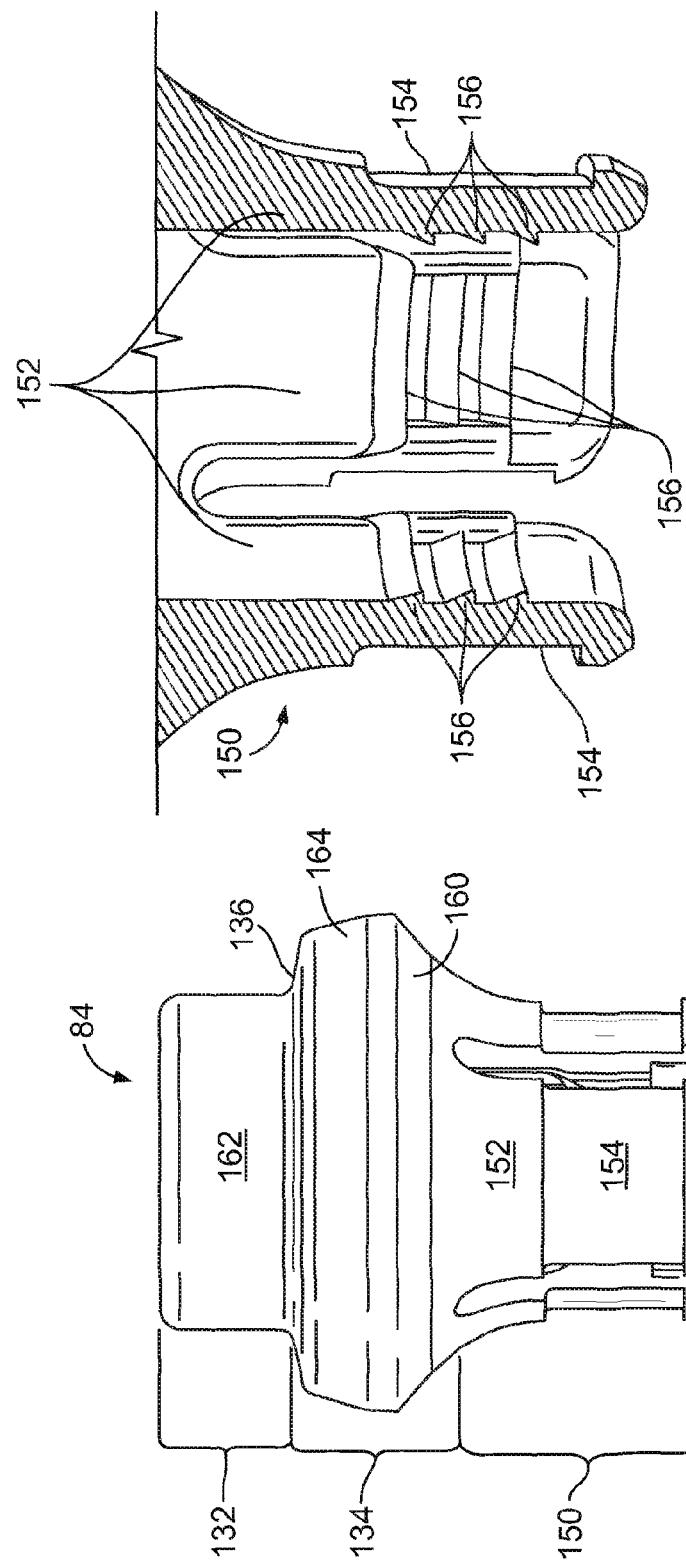

BEARING FOR UMBILICUS OF A FLUID PROCESSING SYSTEM

CROSS-REFERENCE TO RELATED APPLICATIONS

This application claims the benefit of U.S. Non-Provisional patent application Ser. No. 14/693,518 filed Apr. 22, 2015, which issued on Jan. 17, 2017 as U.S. Pat. No. 9,545,637, which is expressly incorporated herein by reference in its entirety.

FIELD OF THE DISCLOSURE

The present disclosure is directed to a bearing and bearing assembly for supporting an umbilicus used, for example, in a fluid processing system.

BACKGROUND

Whole blood is routinely separated into its various components, such as red blood cells, platelets, and plasma. In many blood processing systems, whole blood may be drawn from a donor, the particular blood component or constituent removed and collected, and the remaining blood constituents returned to the donor. By thus removing only particular constituents, less time may be needed for the donor's body to return to normal, and donations can be made at more frequent intervals than when whole blood is collected. This may increase the overall supply of blood constituents, such as plasma and platelets, made available for health care.

One method by which whole blood may be separated into its constituents is centrifugation. Whole blood may be passed through a centrifuge after it is withdrawn from, and before it is returned to, the donor. To avoid contamination, the blood may be contained within a sealed, sterile system during the entire centrifugation process. Blood processing systems thus may include a permanent, reusable centrifuge assembly or "hardware" that spins and pumps the blood, and a disposable, sealed and sterile fluid processing or fluid circuit assembly that actually makes contact with the donor's blood. The centrifuge assembly may engage and spin a portion of the fluid processing assembly (often called the centrifuge or separation chamber) during a collection procedure. The blood, however, may make actual contact only with the fluid processing assembly, which may be used only once and then discarded.

It is desirable for blood processing systems to have features that preserve the longevity of hardware and parts as well as optimize the mechanics of the processing procedure.

SUMMARY

According to an exemplary embodiment, the present disclosure is directed to a fluid circuit for use with a fluid processing assembly, the fluid circuit comprising an umbilicus having a first end, a second end, an axis of rotation, and a cross-sectional circumference. The fluid circuit also comprises a one-piece bearing secured to the umbilicus at a location between the first and second ends, the bearing having an axis of rotation and including an inner lumen which directly engages the umbilicus and includes a plurality of traction features, which bear against the umbilicus to prevent relative rotation of the bearing and the umbilicus. The plurality of traction features comprises a first traction feature which comprises a first plurality of projections disposed at a first rotational angle about the axis of rotation, the first plurality of projections defining all projections disposed on the first traction feature, and is configured to engage the umbilicus at a first set of lengths between the first and second ends. The plurality of traction features also comprises a second traction feature which comprises a second plurality of projections disposed at a second rotational angle about the axis of rotation, the second plurality of projections defining all projections disposed on the second traction feature, and is configured to engage the umbilicus at a second set of lengths between the first and second ends.

According to an exemplary embodiment, the present disclosure is directed to a fluid circuit for use with a fluid processing assembly, the fluid circuit comprising an umbilicus having a first end, a second end, an axis of rotation, and a cross-sectional circumference; a one-piece bearing secured to the umbilicus at a location between the first and second ends, the bearing having an axis of rotation and including an inner lumen which directly engages the umbilicus and includes a plurality of tabs disposed about the axis of rotation of the umbilicus. The plurality of tabs comprises a first tab, disposed at a first rotational angle about the axis of rotation, having a first set of traction features disposed at a first set of lengths between the first and second ends, the first set of traction features defining all traction features disposed on the first tab, wherein the first tab is configured to engage the umbilicus at a first arrangement of compression locations between the first and second ends of the umbilicus. The plurality of tabs also comprises a second tab disposed at a second rotational angle about the axis of rotation, having a second set of traction features disposed at a second set of lengths between the first and second ends, the second set of traction features defining all traction features disposed on the second tab, wherein the second tab is configured to engage the umbilicus at a second arrangement of compression locations between the first and second ends of the umbilicus. The plurality of tabs also comprises a third tab disposed at a third rotational angle about the axis of rotation, having a third set of traction features disposed at the first set of lengths between the first and second ends, the third set of traction features defining all traction features disposed on the third tab, wherein the third tab is configured to engage the umbilicus at the first arrangement of compression locations between the first and second ends of the umbilicus. The plurality of tabs also comprises a fourth tab, disposed at a fourth rotational angle about the axis of rotation, having a fourth set of traction features disposed at the second set of lengths between the first and second ends, the fourth set of traction features defining all traction features disposed on the fourth tab, wherein the fourth tab is configured to engage the umbilicus at the second arrangement of compression locations between the first and second ends of the umbilicus.

According to an exemplary embodiment, the present disclosure is directed to a fluid circuit for use with a fluid processing assembly, the fluid circuit comprising an umbilicus having a first end, a second end, an axis of rotation, and a generally circular cross-section having a circumference. The fluid circuit also comprises a one-piece bearing secured to the umbilicus at a location between the first and second ends, the bearing having an axis of rotation and including an inner lumen which directly engages the umbilicus and includes a plurality of traction features, which bear against the umbilicus at compression locations to prevent relative rotation of the bearing and the umbilicus. The plurality of traction features comprises a first traction feature which comprises a first plurality of projections disposed at a first rotational angle about the axis of rotation, the first plurality of projections defining all projections disposed on the first traction feature, and is configured to engage the umbilicus at a first arrangement of compression locations at a first set of lengths between the first and second ends of the umbilicus. The plurality of traction features also comprises a second traction feature which comprises a second plurality of projections disposed at a second rotational angle about the axis of rotation, the second plurality of projections defining all projections disposed on the second traction feature, and is configured to engage the umbilicus at a second arrangement of compression locations at a second set of lengths between the first and second ends of the umbilicus. The plurality of traction features also comprises a third traction feature which comprises a third plurality of projections disposed at a third rotational angle about the axis of rotation, the third plurality of projections defining all projections disposed on the third traction feature, and is configured to engage the umbilicus at a third arrangement of compression locations at the first set of lengths between the first and second ends of the umbilicus. The plurality of traction features also comprises a fourth traction feature which comprises a fourth plurality of projections disposed at a fourth rotational angle about the axis of rotation, the third plurality of projections defining all projections disposed on the third traction feature, and is configured to engage the umbilicus at a fourth arrangement of compression locations at the second set of lengths between the first and second ends of the umbilicus. The cross-sectional shape of the umbilicus at any compression location within the first, second, third, and/or fourth arrangement of compression locations is non-circular.

BRIEF DESCRIPTION OF THE DRAWINGS

Features, aspects, and advantages of the present embodiments will become apparent from the following description, appended claims, and the accompanying exemplary embodiments shown in the drawings, which are briefly described below.

FIG. 5 is a perspective detail view of a bearing support of the centrifuge of FIG. 4, according to an exemplary embodiment;

FIG. 6 is a perspective view of an umbilicus bearing assembly, according to an exemplary embodiment;

FIG. 7 is an exploded view of the umbilicus bearing assembly of FIG. 6, according to an exemplary embodiment;

FIG. 14 is a front elevational view of the bearing of FIG. 13, according to an exemplary embodiment;

FIG. 15 is a cross-sectional perspective detail view of a retainer portion of the bearing of FIG. 13 for engaging or gripping an umbilicus (not shown) that extends through the bearing, according to an exemplary embodiment;

DETAILED DESCRIPTION

Figure 1:
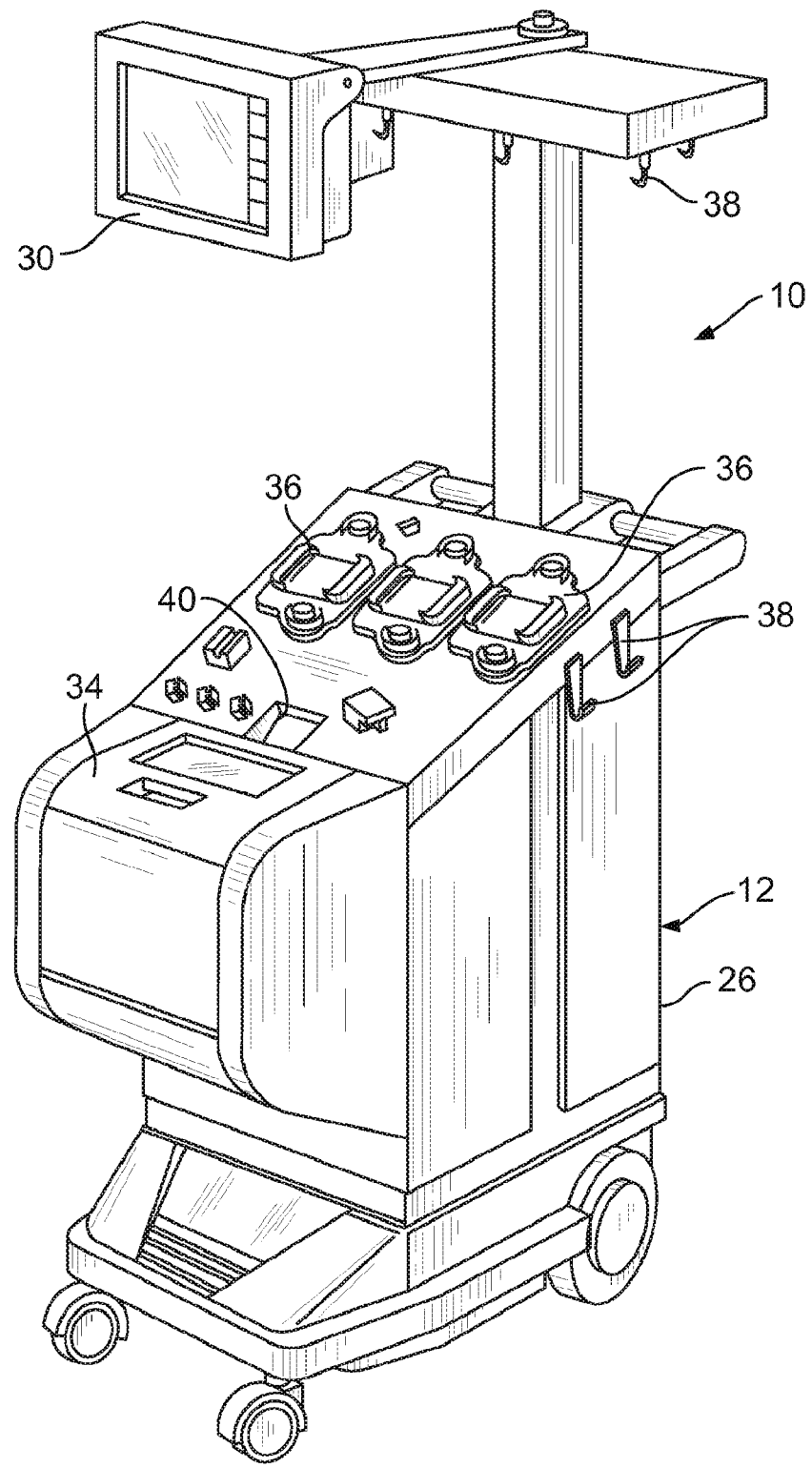
FIG. 1 is a perspective view of a fluid processing system in which bearing assemblies may be employed, according to an exemplary embodiment.

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

To avoid the need for rotating seals, and to preserve the sterile and sealed integrity of the fluid processing assembly, blood processing systems may often utilize centrifuges that operate on the "one-omega, two-omega" operating principle. This principle is disclosed in detail in U.S. Pat. No. 4,120,449 to Brown et al., which is hereby incorporated by reference in its entirety, and enables centrifuges to spin a sealed, closed system without the need for rotating seals and without twisting the components of the system. Blood processing systems that make use of the principle may typically include a fluid processing assembly that includes a plastic bag or molded chamber that is spun in the centrifuge and that is connected to the blood donor and to a stationary portion of the centrifuge assembly through an elongated member that may be made up of one or more plastic tubes. The elongated member is commonly referred to as an "umbilicus" and may typically be arranged in a question mark (or upside-down question mark) configuration with both of its end portions coaxially aligned with the axis of rotation of the centrifuge. The centrifuge chamber may be rotated at "two-omega" RPM and the umbilicus may be orbited around the centrifuge chamber at "one-omega" RPM. That is, one end of the umbilicus may be stationary, the other end may rotate at a two-omega speed with the centrifuge chamber to which it is attached, and the intermediate portion or midsection of the umbilicus may orbit about the chamber at a one-omega speed. The effect is that the end of the umbilicus, which may be opposite the bag or chamber and may be connected to the donor via plastic tubing, may not twist up as the bag is spun. The sealed, sterile integrity of the fluid processing assembly may thus be maintained without the need for rotating seals.

U.S. Pat. No. 5,989,177 to West et al. and U.S. Pat. No. 6,344,020 to Reitz et al., both of which are hereby incorporated herein by reference in their entireties, disclose one such blood processing apparatus based on the "one-omega, two-omega" operating principle. In this apparatus, a disposable fluid processing assembly having an umbilicus and a processing chamber may be mountable within a centrifuge assembly. One end of the umbilicus may be held rotationally stationary substantially coaxial with the axis of centrifugal rotation. The other end of the umbilicus may join the processing chamber and rotate with the processing chamber around the axis of centrifugation at the two-omega speed, up to about 3,000 RPM. The mid-portion of the umbilicus may be supported by a wing plate that rotates around the axis of centrifugation at the one-omega speed, up to about 1,500 RPM. A thrust bearing mounted on the umbilicus may permit the umbilicus to rotate relative to the wing plate as the wing plate and the processing chamber turn at different speeds. The thrust bearing may slide into a one piece gimbal mounted in a recess provided on the wing plate. The gimbal may help keep the fluid processing assembly properly positioned during the centrifugation procedure. When the procedure is completed, the thrust bearing may be slid out of the gimbal in the wing plate to permit removal of the fluid processing assembly.

FIG. 1 shows a centrifugal fluid processing system 10 that may be used in combination with an umbilicus bearing assembly according to the present disclosure. The system is currently marketed as the AMICUS® separator by Fenwal, Inc. of Lake Zurich, Ill. The system 10 may be used for processing various fluids, but is particularly well-suited for processing whole blood, blood components, or other suspensions of biological cellular materials. The system 10 includes a centrifuge assembly 12 for separating a fluid into its constituent parts. A more detailed description of the centrifuge assembly 12 and the other elements of the system 10 can be found in U.S. Pat. No. 5,996,634, which is incorporated by reference herein in its entirety.

Figure 2:
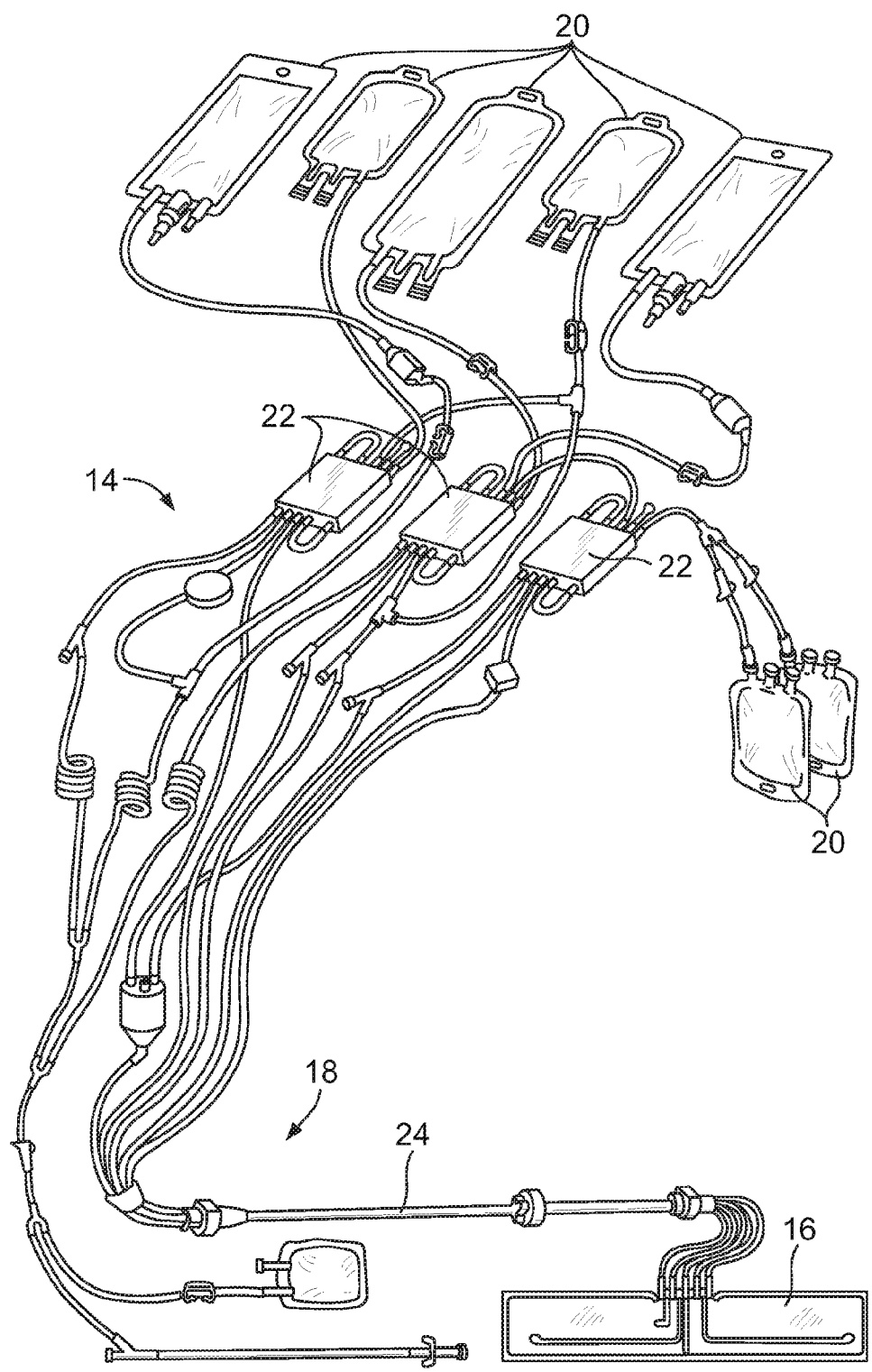
FIG. 2 is a perspective view of a disposable fluid processing or fluid circuit assembly usable in association with the fluid processing system of FIG. 1, according to an exemplary embodiment.
Figure 3:
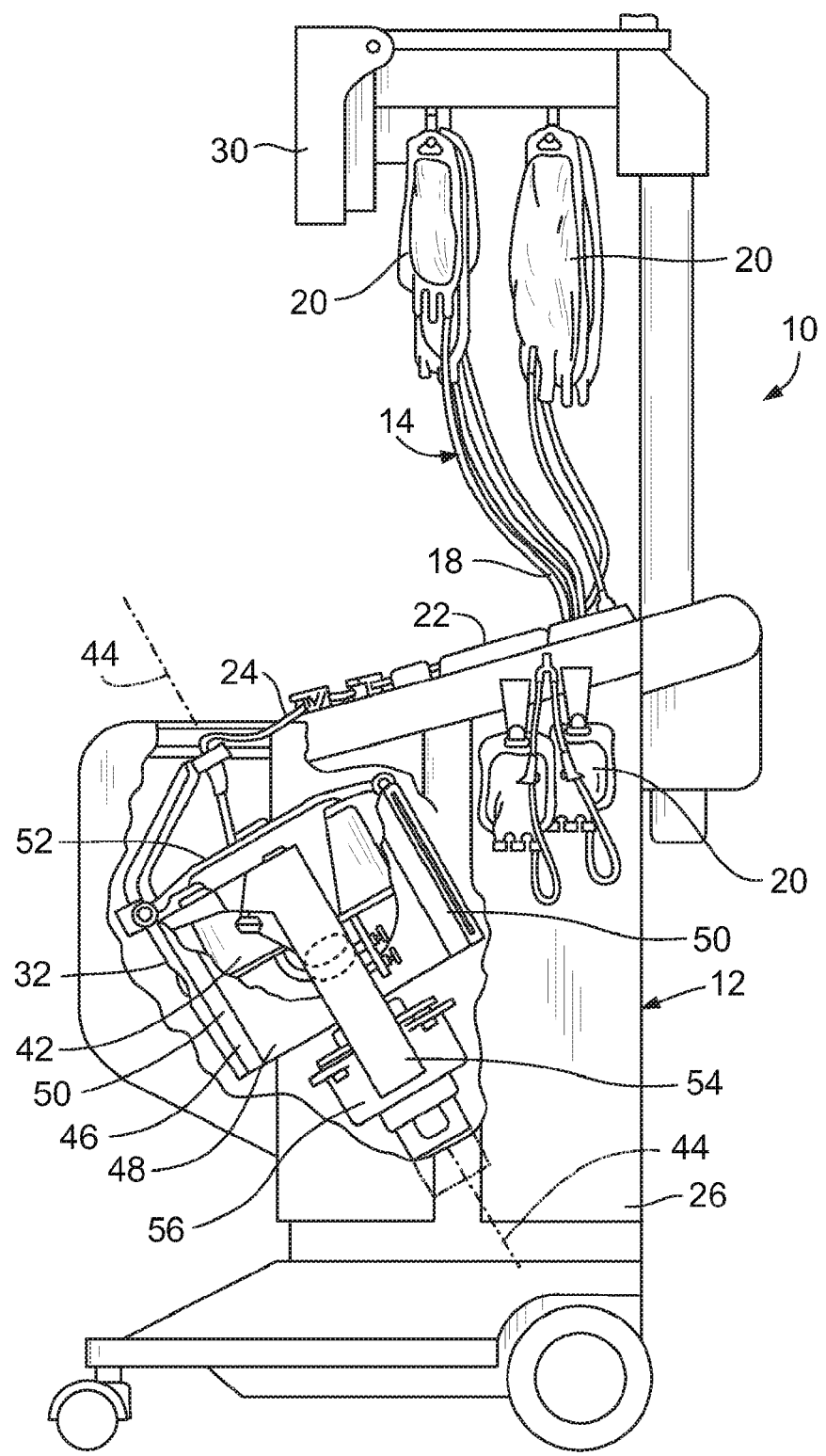
FIG. 3 is a side elevational view of the disposable fluid processing assembly of FIG. 2 mounted on the fluid processing system of FIG. 1, which is partially broken away, according to an exemplary embodiment.

The durable fluid processing system 10 may be used in combination with a disposable processing set or fluid circuit 14, an example of which is shown in FIG. 2. FIG. 3 shows the disposable set 14 mounted on the durable system 10. The disposable set 14 may be a single use, disposable item loaded on the system 10 at the time of use. After a fluid processing procedure has been completed, the operator may remove the disposable set 14 from the system 10 and discard it.

The disposable set 14 includes a processing chamber 16 (FIG. 2). In use, the centrifuge assembly 12 may rotate the processing chamber 16 to centrifugally separate blood components. Whole blood may be conveyed to the processing chamber 16, and separated blood components may be conveyed from the processing chamber 16, through a plurality of flexible tubes that form part of a fluid circuit 18. The fluid circuit 18 may further include a plurality of containers 20 that may be supported by elevated hangers located over the centrifuge assembly 12 (see FIG. 3) and that dispense and receive liquids during processing. Fluid flow through the fluid circuit 14 may be controlled in a variety of ways. Fluid flow may be controlled via cassettes 22 with pre-formed fluid passageways, which may be selectively opened and closed pneumatically, hydraulically, or by movable actuators. The number of cassettes may vary, but in the illustrated embodiment, there are three cassettes 22, which may operate in association with valve and pump stations on the centrifuge assembly 12 to direct liquid flow among multiple liquid sources and destinations during a blood processing procedure. Tubes connected to the processing chamber 16 may lead to a flexible umbilicus 24, with additional tubes at the other end of the umbilicus 24 fluidly connecting the processing chamber 16 (via the umbilicus 24) to the remainder of the disposable set 14, including the containers 20 and the cassettes 22. The disposable set 14 may be a pre-assembled closed system, assuring an operator that it is a sterile unit.

As illustrated, the centrifuge assembly 12 may include a wheeled cabinet 26 that can be easily rolled from place to place. A user-actuable processing controller 30 may be provided which enables the operator to control various aspects of the blood processing procedure. A centrifuge rotor assembly 32 may be provided behind a fold open door 34 that can be pulled open at the front of the cabinet 26 (FIG. 3). A plurality of valve and pump stations 36 (FIG. 1) may be provided on the top face of the cabinet for receiving and controlling the various cassettes 22. A plurality of hooks or hangers 38 may be provided on the cabinet 26 for suspending the various containers 20.

Figure 4:
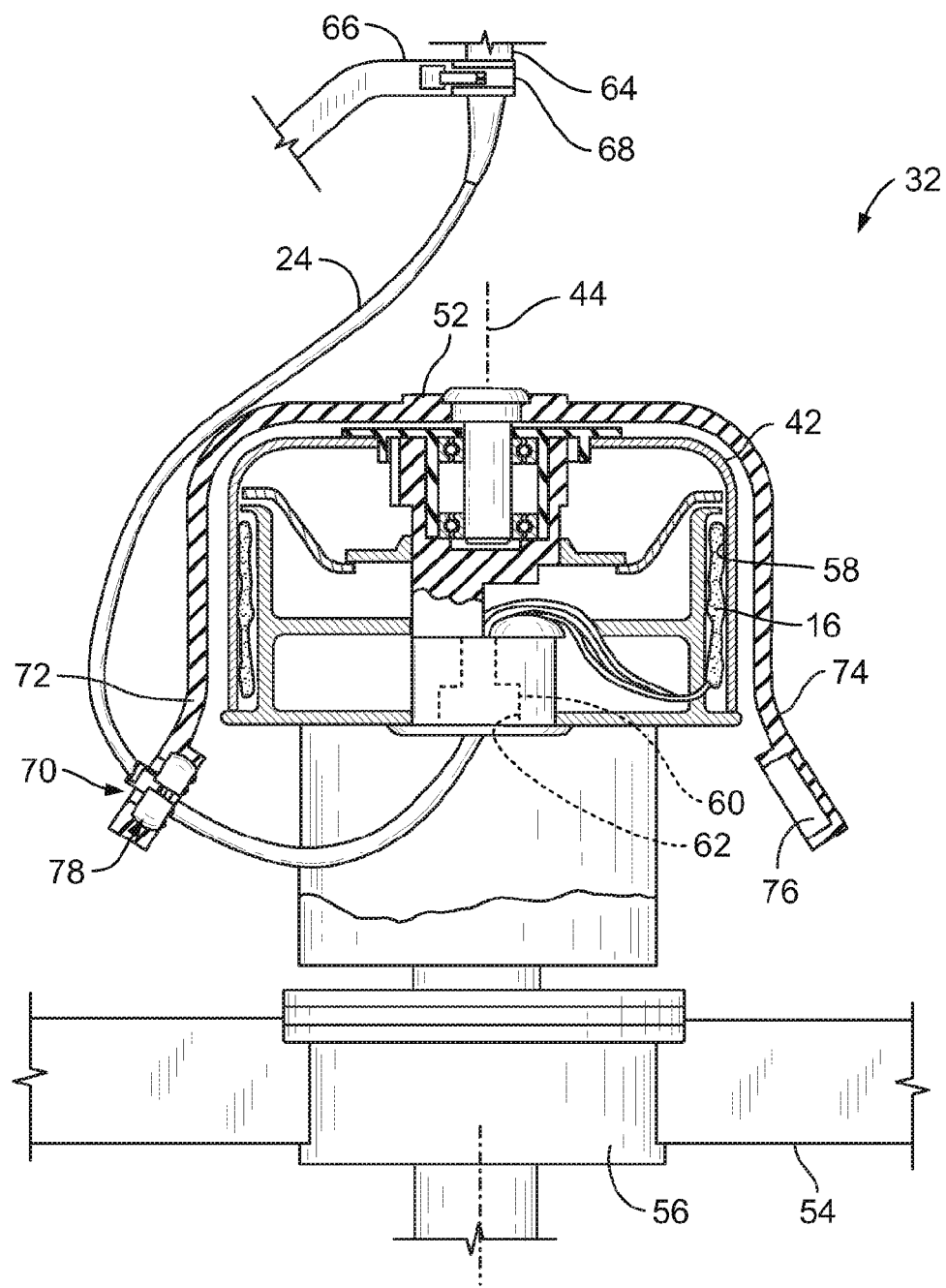
FIG. 4 is a side detail view of a centrifuge included in the fluid processing system of FIG. 1, showing the centrifuge in combination with an umbilicus of the disposable fluid processing assembly, according to an exemplary embodiment.

In use, the fold open door 34 may be opened and the processing chamber 16 of the disposable set 14 may be mounted in the centrifuge rotor assembly 32 (FIG. 4). The umbilicus 24 may be threaded through the centrifuge rotor assembly 32 and out through an opening 40 in the upper panel of the cabinet 26 (FIG. 3). The cassettes 22 may be snapped into respective ones of the valve and pump stations 36 and the containers 20 may be hung from the appropriate hangers 38 (FIG. 3). After appropriate connections are made to the donor using known intravenous techniques, the operator may enter appropriate commands on the processing controller 30 to begin the processing procedure.

Referring to the centrifuge rotor assembly 32 (FIG. 4), it may include a chamber assembly 42 that may be supported for rotation around an axis of centrifugation 44. The centrifuge may further include a centrifuge yoke assembly 46 that includes a yoke base 48, a pair of upstanding yoke arms 50, and a yoke cross member 52 mounted between the arms 50. The yoke base 48 may be rotatably supported on a stationary platform 54 that carries the rotating mass of the centrifuge rotor assembly 32. The yoke base 48 may also be supported for rotation around the axis of centrifugation independently of the chamber assembly 42. An electric drive 56 may rotate the yoke assembly 46 relative to the stationary platform 54 around the axis of centrifugation 44. The chamber assembly 42 may be free to rotate around the axis of centrifugation 44 at a rotational speed that may be different from the rotational speed of the yoke assembly 46.

Referring further to FIG. 4, the chamber assembly 42 may define an annular chamber 58, centered around the axis of centrifugation 44, for receiving the processing chamber 16 of the disposable set 14. The umbilicus 24 may extend through the lower center of the chamber assembly 42 in alignment with the axis of centrifugation 44. A first anchor portion 60 integrally molded or otherwise mounted onto the umbilicus 24, may be received in a lowermost umbilicus mount 62 located at the lower center of the chamber assembly 42. The first anchor portion 60 and umbilicus mount 62 may function to transfer torque between the umbilicus 24 and chamber assembly 42 so that the chamber assembly 42 may rotate around the axis of centrifugation in response to twisting of the umbilicus 24 around its axis.

The other end of the umbilicus 24 may be supported by means of a second anchor portion 64 that may be removably received in an upper umbilicus mount 66 positioned over the centrifuge chamber assembly 42 substantially in alignment with the axis of centrifugation 44. An over-center clamp 68 at the end of the upper umbilicus mount 66 may clamp onto the second anchor portion 64 to hold the adjacent segment of the umbilicus 24 rotationally stationary and in collinear alignment with the axis of centrifugation 44. The second anchor portion 64 may be integrally molded or otherwise securely joined with the umbilicus 24.

As further illustrated in FIG. 4, the portion of the umbilicus 24 between the second anchor portion 64 and the first anchor portion 60 may be supported by a middle umbilicus mount or bearing support 70 (illustrated in greater detail in FIG. 5) that may be carried at the lower end of a wing plate 72 extending outwardly and downwardly from the yoke cross member 52. As the electric drive 56 rotates the centrifuge yoke assembly 46 (FIG. 3) around the axis of centrifugation 44, the wing plate 72 and the bearing support 70 may pull the midsection of the umbilicus 24 around the axis of centrifugation 44 as well. As the umbilicus 24 orbits around the axis 44, at rotational speed one-omega, a twisting action may be imparted to the umbilicus 24 around its own axis. The midsection of the umbilicus 24 may be free to rotate around its own axis relative to the wing plate 72 as the yoke assembly 46 is turned, so it may tend to "untwist" against the twisting motion imparted by the rotating yoke assembly 46. As it untwists in this manner, the umbilicus 24 may spin the centrifuge chamber assembly 42 around the axis of centrifugation 44 at an average rotational speed of two omega.

To maintain balance as the yoke assembly 46 turns, an additional wing plate 74 may extend from the yoke cross member 52 diametrically opposite the wing plate 72. A counterweight 76 sufficient to balance the mass of the bearing support 70 and umbilicus 24 may be carried on the lower end of the additional wing plate 74.

In accordance with one aspect of the present disclosure, the midsection of the umbilicus 24 may be supported on the wing plate 72 by means of an umbilicus bearing assembly 78, which is shown in greater detail in FIGS. 6 and 7. The illustrated umbilicus bearing assembly 78 may include, as illustrated, several distinct parts, one or more of which may be provided as integral combinations with other parts. Specifically, the assembly may include a gimbal or liner receptacle 80, a liner or bearing receptacle 82 at least partially received within the gimbal 80, a one-piece bearing 84 at least partially received within the liner 82, and a retaining member 86 which may secure the bearing 84 within the liner 82. Additionally, fasteners 88 may be provided to secure the gimbal 80 to the liner 82 and a clip 90 in the form of a compression band or other suitable structure may be provided to secure the bearing 84 to the umbilicus 24.

The gimbal 80 of the umbilicus bearing assembly 78 may be received within the bearing support 70, which is shown in greater detail in FIG. 5. The bearing support 70 may comprise a circular opening 92 formed in the lowermost end of the wing plate 72. The side wall 94 of the circular opening 92 may be concavely shaped, thereby giving the opening 92 a generally spherical shape. A gap 96 may be formed in the end of the wing plate 72 and may open into the circular opening 92 to enable the umbilicus 24 and the umbilicus bearing assembly 78 to be inserted into the opening 92 from the side. A pair of orthogonally oriented pivot pins 98 may extend from the side wall 94 of the circular opening 92 towards its center.

Figure 8:
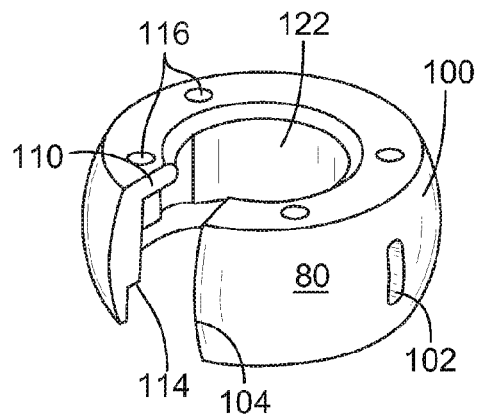
FIG. 8 is a perspective view of a gimbal of the umbilicus bearing assembly of FIG. 6, according to an exemplary embodiment.

The gimbal 80 (FIG. 8) may comprise a "C-shaped" member having a generally annular or ring-like form. The outer surface 100 of the illustrated gimbal 80 may be outwardly rounded or convex, thereby giving the gimbal 80 a generally spherical shape that matches the shape of the opening 92 of the bearing support 70. A pair of elongated slots 102 (only one of which is visible) may be formed through the outer surface 100 and may be positioned and dimensioned to receive the pivot pins 98 when the gimbal 80 is received in the circular opening 92. The rounded outer surface 100 of the gimbal 80, together with the slots 102 and pivot pins 98 received therein, may enable the gimbal 80 to pivot within the circular opening 92 around two orthogonal axes. Such freedom of movement is referred to herein as a "gimbaling" action or motion. A gap 104 may be formed through the side of the gimbal 80 to permit entry of the umbilicus 24. In one embodiment, the gimbal 80 may be formed of a durable, rigid, low-friction plastic such as a Delrin® and/or polytetrafluoroethylene ("PTFE" or Teflon®). While such material may be sufficiently rigid to prevent excessive wear during repeated use (the gimbal 80 being considered a part of the durable fluid processing system 10 and not the disposable set 14), it may be slightly flexed by pinching or squeezing (on account of the thickness of the gimbal wall and the presence of the gap 104) so as to be pressed into the circular opening 92 of the bearing support 70.

Similar to the gimbal 80, the liner or bearing receptacle 82 (FIGS. 9 and 10) may comprise a generally "C-shaped" structure with a gap 106 opening through its side to permit passage of the umbilicus 24 during installation. As with the gimbal 80, the liner 82 may be a reusable component of the umbilicus bearing assembly 78 which may be intended for repeated use as part of the durable fluid processing system 10. Although shown as a separate part, the liner 82 may be integral and of one-piece construction with the gimbal 80. The combination of the gimbal 80 and liner 82 (whether provided separately or integrally) is referred to herein as a gimbal assembly.

Figure 11:
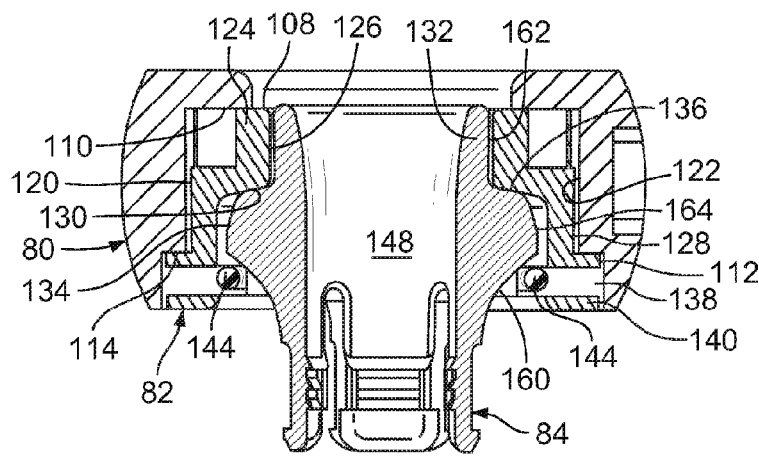
FIG. 11 is a cross-sectional view of the umbilicus bearing assembly of FIG. 6, according to an exemplary embodiment.

The liner 82 may be configured to be at least partially received within the gimbal 80 (FIG. 11). In the illustrated embodiment, a top surface 108 of the liner 82 may abut an upper ledge or transverse wall 110 of the gimbal 80 when the liner 82 is properly positioned within the gimbal 80, thereby providing tactile feedback and a positive stop during assembly. The liner 82 may also include an upper rim 112 which may simultaneously abut a lower ledge or transverse wall 114 of the gimbal 80 when the liner 82 is properly positioned within the gimbal 80. Both the gimbal 80 and the liner 82 may include one or more apertures 116, with each aperture 116 of the gimbal 80 being aligned with a corresponding aperture 116 of the liner 82 when the gap 104 of the gimbal 80 is aligned with the gap 106 of the liner 82. The apertures 116 so aligned may each accommodate a fastener 88 (such as the threaded screws shown in FIGS. 6 and 7) to secure the liner 82 within the gimbal 80. The liner 82 may be secured to the gimbal 80 either before or after the gimbal 80 is installed within the circular opening 92 of the bearing support 70, though it may be advantageous to first install the gimbal 80 so that it is not necessary to squeeze both the gimbal 80 and the liner 82 upon installation of the gimbal 80 into the circular opening 92. It may be advantageous for there to be some amount of lateral clearance between the outer surface 120 of the liner 82 and the inner surface 122 of the gimbal 80. Such a space may expose the outer surface 120 of the liner 82 to the air within the centrifuge 32, thereby potentially reducing the temperature of the liner 82, which may tend to heat up during fluid processing as a result of friction.

Figure 10:
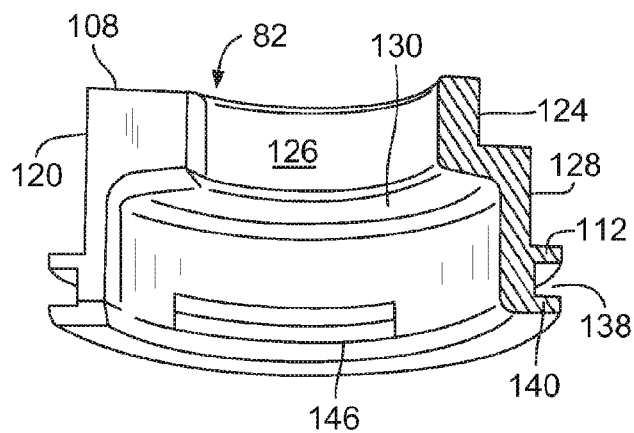
FIG. 10 is a cross-sectional perspective view of the liner of FIG. 9.

The illustrated liner 82 may further include an upper section 124 with a relatively small, substantially constant inner diameter (the surface of which is referred to herein as an axially extending wall 126) and a lower section 128 with a relatively large, substantially constant inner diameter (FIG. 10). The transition between the upper section 124 and the lower section 18 may be defined by a shoulder or radially-extending liner wall 130, which may extend substantially radially or at a selected angle or incline relative to the center axis. The opening defined by the upper section 124 of the liner 82 may be adapted to receive a minor diameter portion 132 of the bearing 84, while the opening defined by the lower section 128 of the liner 82 may be adapted to receive a major diameter portion 134 of the bearing 84, as shown in FIG. 11. The shoulder 130 of the liner 82 may abut a mating bearing surface 136 of the bearing 84 to limit the degree to which the bearing 84 may be inserted into the liner 82 and to provide an arrangement that allows relative rotation between the bearing 84 and the liner 82, while limiting axial movement as a thrust bearing. Such a configuration of the inner surface of the liner 82 may be adapted for use with the bearing 84 illustrated in FIGS. 7 and 11 and it should be understood that a different configuration for the liner inner surface may be more appropriate when the bearing configuration is different.

Figure 9:
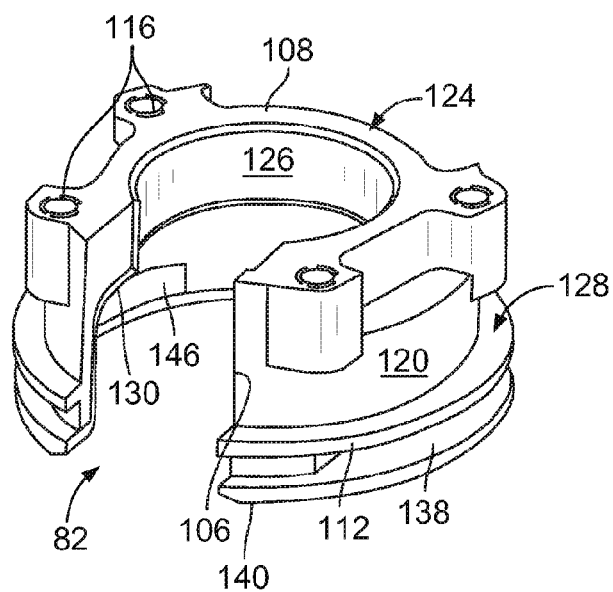
FIG. 9 is a perspective view of a liner that may be received within and form a portion of the gimbal or gimbal assembly of the umbilicus bearing assembly of FIG. 6, according to an exemplary embodiment.
Figure 12:
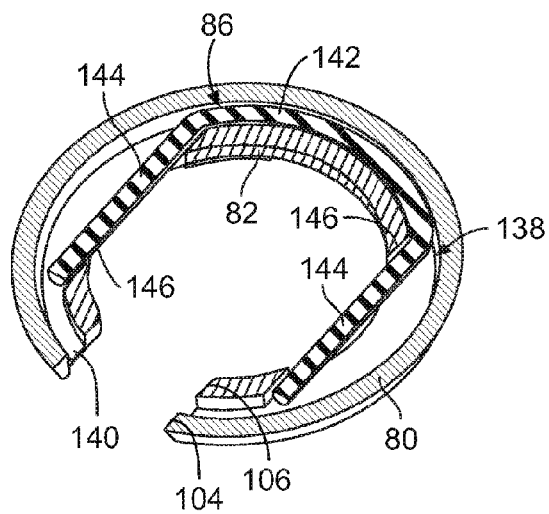
FIG. 12 is a perspective view of a portion of the gimbal, liner, and retaining member of the umbilicus bearing assembly of FIG. 6, according to an exemplary embodiment.

The liner 82 of FIGS. 9-11 may also include a generally "U-shaped" perimeter slot or channel or groove 138, which may be defined between the upper rim 112 and a lower rim 140 adjacent to a bottom end of the liner 82. The channel 138 may receive the retaining member 86, as shown in FIGS. 11 and 12. The illustrated retaining member 86 may include an arcuate crossbeam or cross member 142 (having a curvature substantially the same as the curvature of the channel 138) and a pair of substantially parallel legs 144 extending from the ends of the cross member 142. As shown in FIG. 12, the cross member 142 may be positioned diametrically opposite the gap 106 of the liner 82, with the legs 144 extending from the cross member 142 in the direction of the gap 106. Two opposing lateral passages 146 (best shown in FIGS. 9 and 10) may extend through the wall of the liner 82, allowing a portion of each leg 144 of the retaining member 86 to communicate with the open interior of the liner 82 (FIGS. 11 and 12). The major diameter portion 134 of the bearing 84 may be wider than the separation between the legs 144 (FIG. 11), but the legs 144 may be resilient (being made of a material such as stainless steel or spring steel or the like), thereby allowing the major diameter portion 134 of the bearing 84 to press the legs 144 away from each other as the bearing 84 is pressed into the liner 82. When the major diameter portion 134 has passed beyond the legs 144 and into the liner 82, the legs 144 may resiliently return to their original straight configuration (FIGS. 11 and 12), thereby temporarily securing the bearing 84 within the liner 82. Such a configuration may provide a tactile and audible indication that the bearing 84 has been successfully loaded into the liner 82.

In one embodiment, the liner 82 may be formed of a durable, high stiffness material such as stainless steel. A metallic material may be advantageous for drawing away from the bearing 84 any heat arising from friction generated between the liner 82 and the bearing 84 during fluid processing. Stainless steel may be advantageous due to its low corrosion nature and ability to accept a wide range of coatings for further reducing friction between the interior of the liner 82 and the exterior of the bearing 84. Among such low friction coatings are polyether ether ketone ("PEEK"), diamond-chrome, and nickel-boron nitride. A PEEK coating may be advantageous because of its low coefficient of friction, durability, and ability to withstand high temperatures. Hence, it may be most advantageous to provide the liner 82 as a stainless steel component having an inner surface which is at least partially coated with PEEK. However, other materials, including solid polymers, may also be used without departing from the scope of the present disclosure.

Figure 13:
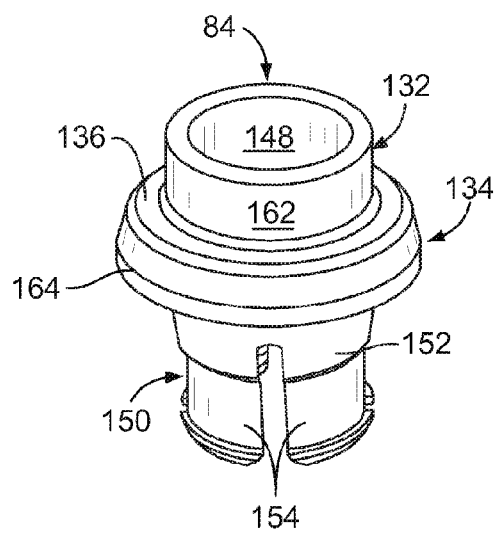
FIG. 13 is a perspective view of the one-piece bearing of the umbilicus bearing assembly of FIG. 6, according to an exemplary embodiment.

The one-piece bearing 84 (FIGS. 13 and 14) may generally be tubular, with an inner lumen or surface 148 defining an open interior sufficiently sized to accommodate the umbilicus 24. During assembly of the disposable set 14, the bearing 84 may be slid axially or longitudinally onto and along the umbilicus 24 to a position between the anchor portions 60, 64. The bearing 84 may be slid into place before one or both of the anchor portions 60, 64 is associated with the umbilicus 24, or otherwise the presence of the anchor portions 60, 64 would prevent proper positioning of the bearing 84. The bearing 84 may be oriented with its minor diameter portion 132 facing the upper anchor portion 64 and an attachment portion or flange portion 150 facing the lower anchor portion 60. The location of the bearing 84 on the umbilicus 24 is referred to herein as a midsection of the umbilicus 24, although the bearing 84 may not necessarily be located at the midpoint between the upper and lower anchor portions 64 and 60.

It may be advantageous for the inner diameter of the bearing 84 to be substantially the same as the outer diameter of the umbilicus 24 to ensure that the umbilicus 24 fits snugly around the bearing 84, thereby preventing radial or lateral movement of the umbilicus 24 within the bearing 84. It may also be advantageous for one end of the inner lumen 148 of the bearing 84 (illustrated in FIG. 11 as the top end) to be outwardly tapered to help guide the umbilicus 24 into the bearing 84 during assembly. Additionally, as the umbilicus 24 may tend to bend in the region of the bearing support 70 during fluid processing, such a taper may provide a smooth surface to interface with a bending umbilicus 24, thereby reducing stress and easing the shear forces experienced by the bending umbilicus 24 at that location.

The inner lumen 148 of the bearing 84 may be held in place against the umbilicus 24 by any of a number of acceptable means, including an adhesive or other bonding agent and/or a physical restraint. In the embodiment illustrated in FIGS. 6 and 7, the bearing 84 may be secured to the umbilicus 24 by means of a compression band or clip 90 (FIGS. 6 and 7). More particularly, the flange portion 150 of the bearing 84 (illustrated as a bottom end of the bearing 84 in FIGS. 13 and 14) may include a plurality of spaced-apart flanges or tabs 152 which may be forced radially inwardly toward a central axis of the bearing 84. Each flange 152 may have an indentation 154 on its outer surface, which indentations 154 may align to form an annular seat for the clip 90. The clip 90 may have a smaller inner diameter than the lower end of the bearing 84, so when it is pushed into contact with the lower end of the bearing 84 (upwardly in the orientation of FIG. 7), it may force the flanges 152 radially inwardly, eventually seating within the indentations 154. The flanges 152 may grip the umbilicus 24, thereby preventing the bearing 84 from moving with respect to the umbilicus 24.

Figure 15A:
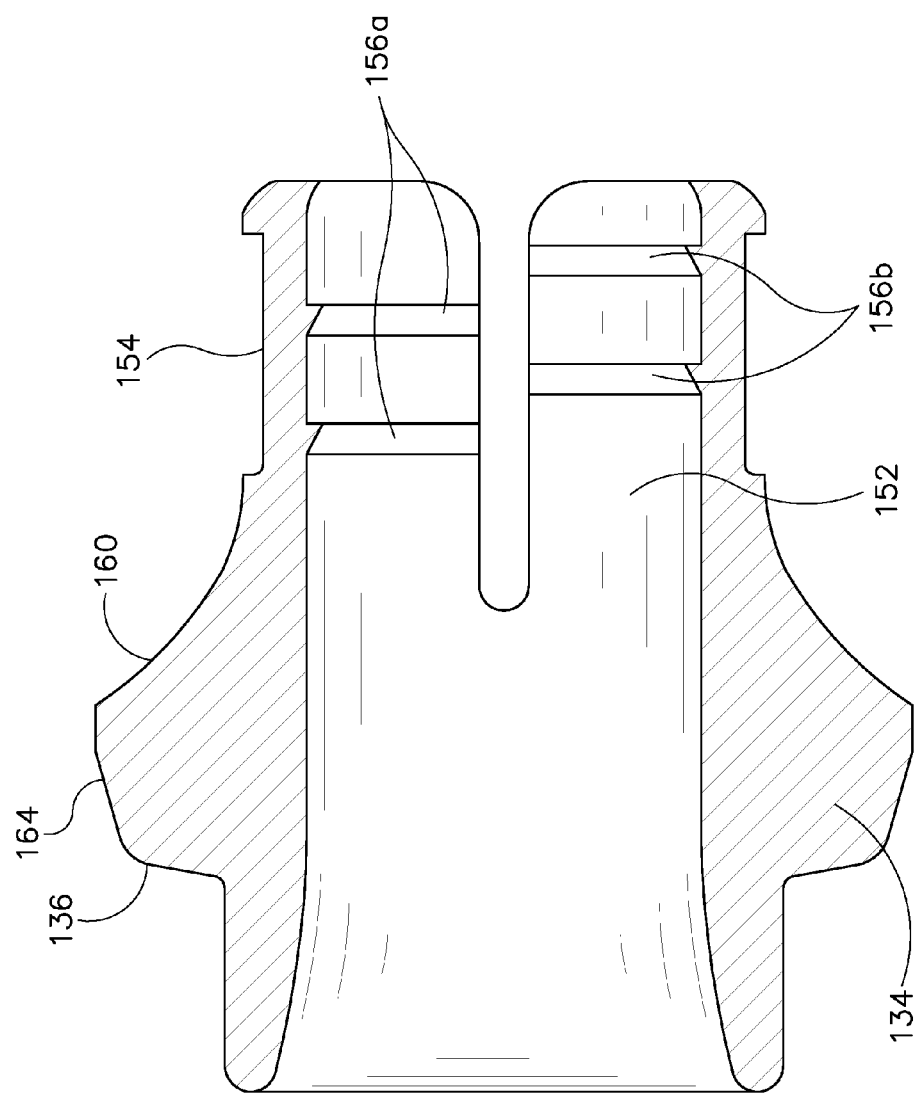
FIG. 15A is a cross-sectional perspective detail view of a retainer portion of the bearing of FIG. 13 for engaging or gripping an umbilicus (not shown) that extends through the bearing, according to another exemplary embodiment.

The inner surfaces of the flanges 152 may include additional features to promote a secure grip by increasing the force required to cause the bearing 84 to slip axially along the umbilicus 24. For example, FIG. 15 shows one embodiment wherein the inner surface of each flange 152 may include a traction feature comprised of a plurality of parallel projections or barbs 156 which are oriented transverse to the central axis of the bearing 84. FIG. 15A shows another embodiment wherein the inner surface of each flange 152 may include a traction feature comprised of a plurality of projections or barbs (156a and 156b) which are oriented transverse to the central axis of the bearing 84 and also oriented in a staggered configuration with respect to projections or barbs 156a, 156b in adjacent flanges 152. As used herein, the term "staggered configuration" refers to traction features, such as 156a and 156b, that are staggered such that they are not positioned at identical locations along the longitudinal axis of the bearing 84. A staggered configuration as shown in FIG. 15A results in a secure grip which minimizes slippage not only longitudinally along the length of the umbilicus 24, but also rotationally about the central axis of the umbilicus 24 and bearing 84. Rotational slippage may occur as the reactant force of the umbilicus 24 to the bearing 84 decays over time. Minimizing rotational slippage, which is sometimes due to the necking down (diameter reduction) of the umbilicus 24 to the bearing 84 over time due to the axial load induced by the umbilicus 24 rotating in the g-field for an extended period of time, is desirable to maximize the longevity of the umbilicus 24 during the fluid processing procedure, as extended rotation of the bearing 84 relative to the umbilicus 24 may cause the barbs 156 to cut into the material of the umbilicus 24. Minimizing rotational slippage can therefore also prevent leakage of the fluid through the umbilicus 24.

Figure 15B:
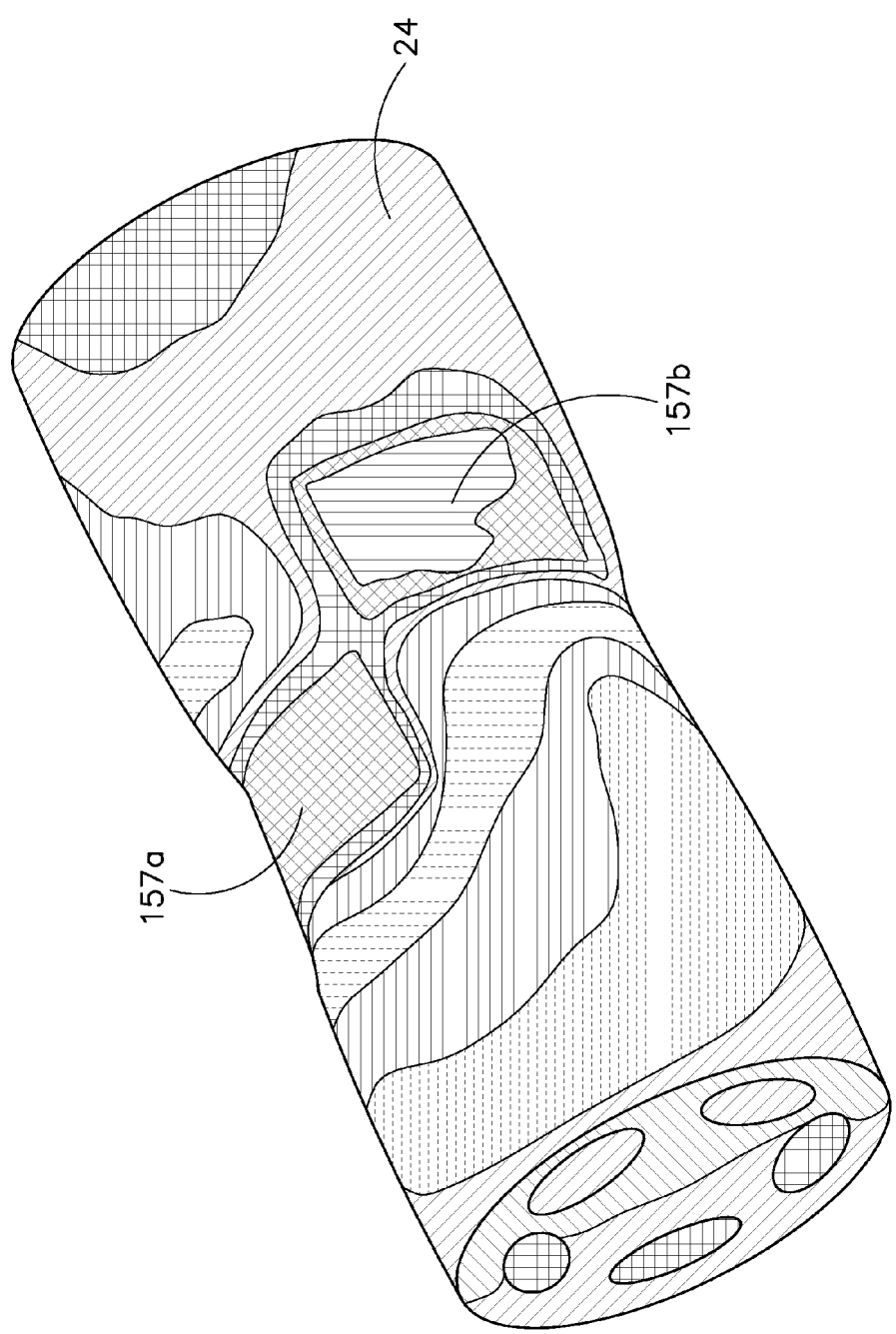
FIG. 15B is a perspective view of the shape of the umbilicus fitted within the bearing shown in FIG. 15A, according to an exemplary embodiment.

FIG. 15B illustrates an embodiment of the shape of the umbilicus 24 fitted within the embodiment of the bearing shown in FIG. 15A. The umbilicus 24 may be made of hytrel or any thermoplastic elastomer, which may take a compressive set after the bearing 84 is clamped onto the umbilicus 24, due to the viscoelastic nature of the material. As FIG. 15B shows, the staggered configuration of the projections or barbs 156a, 156b with respect to adjacent flanges 152 results in the umbilicus 24 having a cross-sectional shape that is oval at the location of compression 157a, 157b between the umbilicus 24 and flanges 152. In one embodiment, the bearing 84 may comprise four flanges or tabs 152 each having a set of barbs 156a, 156b that are staggered relative to adjacent tabs 152 but aligned relative to non-adjacent tabs 152. In such an example, a first barb 156a may be aligned with a second barb 156a that is located on a tab 152 diametrically opposed to the tab of the first barb 156a. The first and second barbs 156a may contact the umbilicus 24 in FIG. 15B at two compression locations 157a (only one compression location illustrated), which may be locations diametrically opposed about the cross-section of the umbilicus 24. Simultaneously, a third barb 156b may be aligned with a fourth barb 156b that is located on a tab 152 diametrically opposed to the tab of the third barb 156b (but adjacent to barbs 156a and staggered relative to barbs 156a). The third and fourth barbs 156b may contact the umbilicus 24 at an adjacent cross-sectional point (as shown in FIG. 15B) at two compression locations 157b (only one compression location illustrated), which may be locations diametrically opposed about the umbilicus cross-section. In one embodiment, compression locations 157a and 157b may have a 90 degree relationship to each other about the circumference of the umbilicus cross-section such that the oval cross-sections of the umbilicus that result are 90 degree rotations of each other.

Although an example has been provided for four tabs with barbs in alignment with barbs diametrically opposed, any number of tabs 152 having barbs 156 may be provided, with barb alignment between/among tabs occurring at any angle(s) about the circumference of the cross-section of umbilicus 24. The cross-sectional shape that results may thereby comprise any non-circular shape, including an oval shape. It is also contemplated that any number of adjacent non-circular cross-sectional points may be provided. For example, a single non-circular cross-sectional point may be provided. In such an embodiment, for example in FIG. 15A, only one set of diametrically opposed tabs 152 may include barbs 156a, while the remaining two tabs may have no barbs 157b. The resulting umbilicus 24, for example in FIG. 15B, may have a single oval cross-sectional point to resist rotational slippage by virtue of having only one pair of diametrically opposed compression locations 157a, rather than two pairs.

Figure 15C:
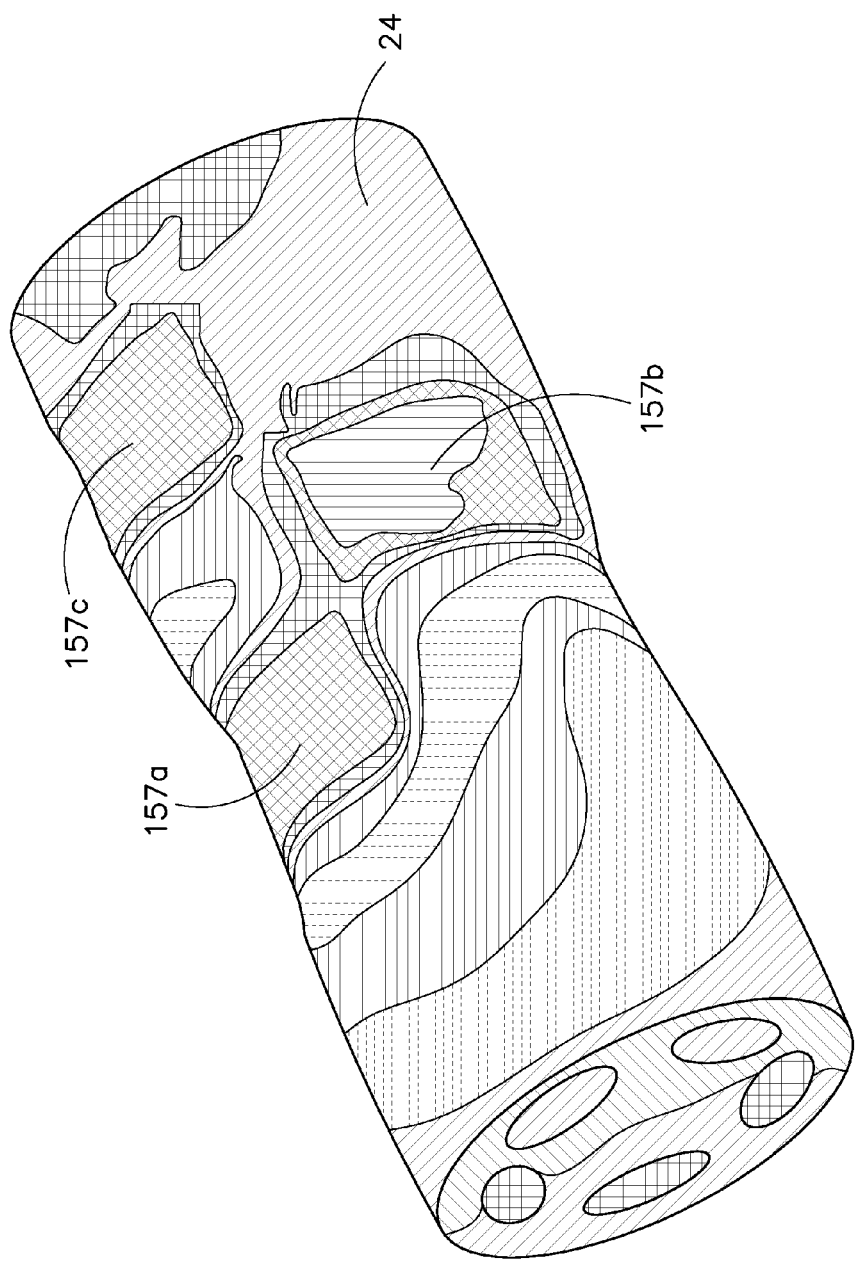
FIG. 15C is a perspective view of the shape of the umbilicus fitted within another embodiment of a bearing, according to an exemplary embodiment.

In another example, three non-circular cross-sectional points may be provided. In this embodiment, at least one set of diametrically opposed tabs 152 may have more than one set of barbs 156 such that a single set of diametrically opposed tabs 152 may provide two pairs of diametrically opposed compression locations 157a and 157c (FIG. 15C) to create two oval cross-sections. In the embodiment of FIG. 15C, the two location pairs 157a and 157c are interposed by compression location pair 157b, which may be created by another set of diametrically opposed tabs 152, each having at least one set of barbs 156b not aligned with any of the two locations pairs 157a and 157c.

In another example, a different number of tabs 152 may be provided such that the cross-sectional shape of the umbilicus 24 that results may not be created by diametrically opposed tabs 152. For example, the bearing 84 may have three tabs 152, in which case no tab may be diametrically opposed to any other tab. In such an embodiment, depending on the configuration and alignment of the barbs 156, each compression location 157a, 157b, or 157c within a pair of compression locations, may have an angular relationship of 120 degrees rather than the diametric relationship of 180 degrees.

Turning now to the outer surface of the one-piece bearing 84, the illustrated embodiment may be comprised of three sections—the minor diameter portion 132, the above-described flange or attachment portion 150, and the major diameter portion 134, which may be positioned between the minor diameter portion 132 and the flange portion 150. The transition from the minor diameter portion 132 to the major diameter portion 134 may be defined by the radially-extending bearing surface 136, which may act as a thrust bearing in an axial direction. The transition from the major diameter portion 134 to the flange portion 150 may be defined by a lead-out surface 160.

The minor diameter portion 132 may be substantially tubular, with an outer surface 162 configured to be received within the opening defined by the axially-extending wall 126 of the liner 82 (FIG. 11). The outer surface 162 of the minor diameter portion 132 is referred to herein as an axially-extending bearing surface and may be acted on by radial forces. In the illustrated embodiment, the diameter of the axially-extending bearing surface 162, while being smaller than the diameter of the axially extending liner wall 126, may be comparable to the diameter of the axially-extending liner wall 126. Such a configuration may have a number of benefits. For example, it may prevent the axially extending bearing surface 162 from binding within the axially-extending liner wall 126. At the same time, the diameters of the axially-extending liner wall 126 and axially-extending bearing surface 162 may be sufficiently close that the axially extending bearing surface 162 may only be allowed a small amount of lateral travel before coming into contact with the axially extending liner wall 126. This may ensure that the bearing 84 remains generally coaxial with the liner 82 during fluid processing for optimal performance.

As for the illustrated major diameter portion 134, it may be comprised of the radially-extending bearing surface 136, a lead-in surface 164, and the lead-out surface 160. The illustrated radially-extending bearing surface 136 may extend from the axially-extending bearing surface 162 in a direction generally away from the central axis of the bearing 84. In use, the radially-extending bearing surface 136 may abut the shoulder 130 of the liner 82 (FIG. 11), with the two being oriented at approximately the same angle to maximize the surface contact therebetween. Such a configuration may have a number of benefits. For one, it may give the bearing 84 a self-centering feature with respect to the liner 82. Further, during use the liner 82 may press against the bearing 84 with an axial force, but an inclined interface therebetween may give the force a radial component, which may effectively reduce the magnitude of the force in the axial direction. In the illustrated embodiment, the shoulder 130 and radially-extending bearing surface 136 may be inclined and oriented approximately 10° from horizontal, sloping away from the associated axially-extending liner wall 126 and axially-extending bearing surface 162, respectively. While the illustrated angle for the radially-extending bearing surface 136 and the shoulder 130 has been found to be advantageous, other configurations and angles may also be employed without departing from the scope of the present disclosure.

The illustrated lead-in surface 164 may extend from an outer end of the radially-extending bearing surface 136 and extend radially outwardly therefrom. As shown in FIG. 11, the lead in surface 164 may be oriented at a sharper incline than the radially extending bearing surface 136. As best illustrated in FIG. 11, the maximum diameter of the radially-extending bearing surface 136 may be approximately equal to or slightly smaller than the separation between the legs 144 of the retaining member 86. Thus, upon pressing the bearing 84 into the liner 82, the radially-extending bearing surface 136 may pass into the liner 82 without contacting the legs 144 of the retaining member 86. The lead-in surface 164, however, may be wider than the separation between the legs 144, so it may contact the legs 144 as the bearing 84 is pressed into the liner 82. Rather than getting caught upon the legs 144, the incline of the lead-in surface 164 may gradually press the legs 144 away from each other and allow the lead-in surface 164 to pass beyond the legs 144 and into the liner 82.

The inclination of the lead-in surface 164 may be varied to determine the force required to press the bearing 84 into the liner 82, with greater inclination (i.e., closer to parallel with the central axis of the bearing 84) tending to allow the bearing 84 to be loaded into the liner 82 at a lower insertion force. For example, in one embodiment the inclination of the lead-in surface 164 may be approximately 15° from parallel with the central axis of the bearing 84. Such an inclination may be sufficiently great that the bearing 84 can be automatically loaded into the liner 82 upon rotation of the umbilicus 24 as part of a fluid processing procedure. It should be noted that, while reference is made to the lead-in surface 164 having an inclination, its configuration is not limited to a strict frusto-conical shape with a uniform inclination. In particular, the illustrated embodiment may have a lead-in surface 164 which is slightly parabolic or defined by a compound angle. Other configurations of the lead-in surface 164 may also be employed without departing from the scope of the present disclosure.

The outer edge of the lead-in surface 164 may mark the transition between the lead-in surface 164 and the lead-out surface 160. In contrast to the lead-in surface 164, the lead-out surface 160 may be inwardly inclined or tapered (i.e., having an outer diameter which decreases as the bearing 84 is inserted into the liner 82). When the lead-in surface 164 has fully passed beyond the legs 144 of the retaining member 86 and the outer diameter of the bearing 84 begins to decrease (i.e., in the region of the lead-out surface 160), the legs 144 may begin to resiliently return to their original straight configuration, pressing toward each other and against the lead-out surface 160. At this point, the bearing 84 may be temporarily secured within the liner 82, as the lead-out surface 160 cannot exit the liner 82 without being pulled (to press the legs 144 of the retaining member 86 far enough apart from each other so as to allow passage of the lead-out surface 160).

In the illustrated embodiment, the lead-out surface 160 may define a greater angle to the central axis of the bearing 84 than the lead-in surface 164, meaning that it may be easier to insert the bearing 84 into the liner 82 than to remove the bearing 84 from the liner 82. For example, in one embodiment, the lead-in surface 164 may be inclined at approximately 15° (from parallel with the central axis of the bearing 84), while the lead-out surface 160 may be inclined at approximately 45°. Such a configuration for the lead-out surface 160 may be advantageous, as it may cause the legs 144 of the retaining member 86 to quickly "snap" back toward their original straight configuration, providing a tactile and audible indication that the bearing 84 has been successfully loaded into the liner 82. Also in the illustrated embodiment, the lead-out surface 160 may be tapered to a small enough outer diameter that the legs 144 of the retaining member 86 may be returned to their original straight configuration when the bearing 84 has been loaded within the liner 82 (FIG. 11). This may be advantageous for a number of reasons (including improving the durability of the retaining member 86), but in other embodiments the lead-out surface 160 may only allow for a partial return of the legs 144 of the retaining member 86 to their original straight configuration upon full insertion of the bearing 84 into the liner 82.

The function of an umbilicus bearing assembly is to associate the umbilicus to the bearing support while allowing the umbilicus to rotate about its own central axis in the region of the bearing support. The one-piece bearing 84 of the present disclosure (particularly the radially-extending bearing surface 136 and the axially-extending bearing surface 162) may effectively slide against the liner 82 for relative rotation. Accordingly, it may be advantageous for the bearing 84 to be comprised of a material having a low coefficient of friction, thereby minimizing the amount of heat generated during use while also ensuring that the umbilicus 24 is free to rotate about its own central axis (as any binding of the bearing 84 within the liner 82 can cause undesirable torsion of the umbilicus 24 during fluid processing). Additional material characteristics of the bearing 84 may also be advantageous. For example, it may be advantageous for the material used to be resistant to abrasion and sufficiently rigid or hard so as to withstand (without deformation) the forces exerted upon the bearing 84 during fluid processing. Another advantageous characteristic may be a high melt temperature, which may prevent wear and softening of the bearing 84 upon reaching the maximum temperature and load during fluid processing. Typically, the disposable set 14 (including the bearing 84) may be sterilized prior to use by way of an electron-beam or gamma sterilization process, in which case it may be advantageous for the bearing material to be able to withstand such a sterilization process without excessive degradation.

Generally speaking, a material having a relatively high density may be suitable for use in forming the one-piece bearing 84. More particularly, selected polyesters (especially reinforced polyesters) may have the desired mechanical characteristics and may perform suitably. Within the family of reinforced polyesters, thermoplastic crystalline polymers may perform particularly well due to their high formability with minimal shrinkage, greater dimensional accuracy and endurance, high rigidity and mechanical strength, high heat stability, and very low electrical conductivity (to minimize the potential for static energy build up during rotation of the umbilicus 24). In one embodiment, the bearing 84 may be injection molded as a single piece using the thermoplastic crystalline polymer polybutylene terephthalate (PBT). It may be advantageous for the polymer base material to include an additive to raise the flexural modulus and heat resistance and to provide increased lubricity. When using a PBT base material, suitable fillers may include (but are not limited to) one or more of: aramid fiber, PTFE/Teflon®, silicone oil or gum, and PEEK. These fillers may work well in varying concentrations to produce the desired results, including ease in injection moldability and high stiffness. In one exemplary formulation, the bearing material may be comprised of approximately 80% PBT, 18% PTFE, and 2% silicone oil or gum.

Alternatively, the material composition of the liner 82 and the bearing 84 may be reversed. For example, the liner 82 may be a molded component comprised of a polymeric material, such as a PBT base material with a filler material (e.g., PTFE and/or silicone oil or gum), while the bearing 84 may be comprised of a metallic material, such as stainless steel with a PEEK coating.

Figures 16, 17:
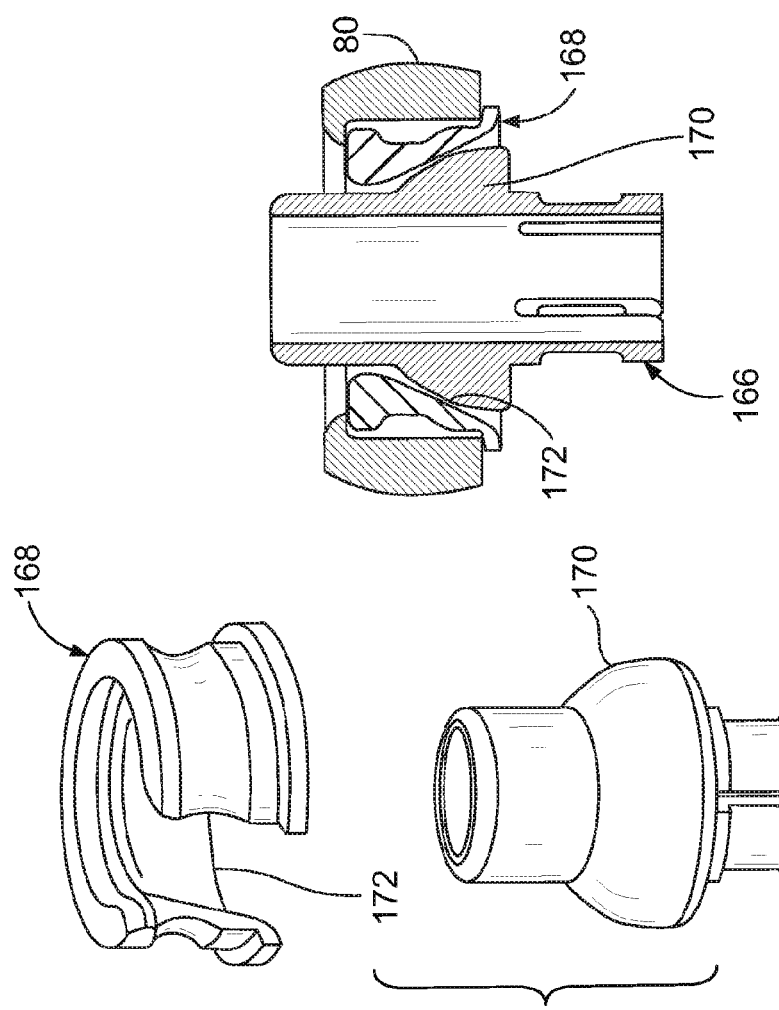
FIG. 16 is an exploded view of an alternative embodiment of a one-piece bearing and gimbal liner, according to an exemplary embodiment.
FIG. 17 is a cross-sectional view of the bearing and liner of FIG. 16 mounted within a gimbal, according to an exemplary embodiment.

An alternative embodiment of a bearing 166 and associated liner 168 according to the present disclosure is shown in FIG. 16, with FIG. 17 showing the bearing 166 and liner 168 being mounted within a gimbal 80 according to the foregoing description. The bearing 166 of FIG. 16 may be substantially the same as the bearing 84 of FIGS. 13 and 14, except for a different major diameter portion 170. Rather than having a radially-extending bearing surface 136, lead-in surface 164, and lead-out surface 160, the major diameter portion 170 of the bearing 166 of FIG. 16 may have a generally hemispherical outer surface. To accommodate such a bearing 166, the inner surface 172 of the liner 168 may define a generally conical or paraboloid open interior (FIG. 17). As in the previous embodiment, the outer surface of the bearing 166 (particularly the major diameter portion 170) may directly engage the inner surface 172 of the liner 168 and effectively slide against the liner 168 for relative rotation.

The embodiment of FIGS. 16 and 17 may also differ from the previous embodiment in that it may omit a retaining member or other means for temporarily securing the bearing 166 within the liner 168. As described previously, bearings according to the present disclosure may have a self-loading function and the bearing, once loaded (whether manually or automatically), may remain in the liner during fluid processing due to the motion of the umbilicus 24, the forces exerted upon the umbilicus 24, and the simple configuration of the bearing and liner. Accordingly, while a retaining member may provide additional security and assurance that the bearing is properly loaded in the liner, it may not be required. Hence, it should be understood that the embodiment of FIGS. 6 and 7 may be practiced without the retaining member 86 and that the embodiment of FIGS. 16 and 17 may be practiced with a retaining means.

Prior to an operator beginning a fluid processing procedure, the gimbal 80 and liner 82, 168 (being part of the durable fluid processing system 10) may already be in place within the bearing support 70 and the bearing 84, 166 may already be secured to the midsection of the umbilicus 24 at the appropriate location. The operator may associate the various components of the disposable set 14 with the corresponding components of the fluid processing system 10 (e.g., hanging the containers 20 on the designated hangers 38 and inserting each cassette 22 into the appropriate valve and pump station 36). The user may fold open the door 34 to gain access to the centrifuge rotor assembly 32 (FIGS. 3 and 4). The user may place the processing chamber 16 in the annular chamber 58 and may clamp the anchor portions 60 and 64 of the umbilicus 24 into their designated mounts 62 and 66. The umbilicus 24 may be inserted sideways through the aligned gaps 96, 104, and 106 of the bearing support 70, gimbal 80, and liner 82, 168, with the bearing 84, 166 being positioned on the liner side of the bearing support 70 (as opposed to the gimbal side of the bearing support 70). The bearing 84, 166 can then be either pressed into the liner 82, 168 or left in place to allow for an automatic loading during fluid processing.

Once the disposable set 14 is in place, the operator may proceed in carrying out a fluid processing procedure (inputting instructions into the controller 30, phlebotomizing a subject, etc.) according to known methods.

The embodiments disclosed herein are for the purpose of providing a description of the present subject matter, and it is understood that the subject matter may be embodied in various other forms and combinations not shown in detail. Therefore, specific embodiments and features disclosed herein are not to be interpreted as limiting the subject matter as defined in the accompanying claims.

The invention claimed is:

1. A fluid circuit for use with a fluid processing assembly, the fluid circuit comprising:
an umbilicus having a first end, a second end, an axis of rotation, and a cross-sectional circumference; a one-piece bearing secured to the umbilicus at a location between the first and second ends, the bearing having an axis of rotation and including an inner lumen which directly engages the umbilicus and includes a plurality of traction features, which bear against the umbilicus to prevent relative rotation of the bearing and the umbilicus; and
wherein the plurality of traction features comprises a first traction feature which comprises a first plurality of projections disposed at a first rotational angle about the axis of rotation, the first plurality of projections defining all projections disposed on the first traction feature, and is configured to engage the umbilicus at a first set of lengths between the first and second ends, and a second traction feature which comprises a second plurality of projections disposed at a second rotational angle about the axis of rotation, the second plurality of projections defining all projections disposed on the second traction feature, and is configured to engage the umbilicus at a second set of lengths between the first and second ends.

2. The fluid circuit of claim 1, wherein the traction features are oriented transversely to the axis of rotation of the bearing and umbilicus.

3. The fluid circuit of claim 1, wherein the cross section of the umbilicus at each length within the first and/or second set has a generally offset ovular shape when engaged by the traction features.

4. The fluid circuit of claim 1, wherein the traction features are disposed on tabs circumferentially disposed about the axis of rotation of the bearing.

5. The fluid circuit of claim 4, further comprising a third traction feature which comprises a third plurality of projections disposed at a third rotational angle about the axis of rotation, the third plurality of projections defining all projections disposed on the third traction feature; and is configured to engage the umbilicus at a third set of lengths between the first and second ends.

6. The fluid circuit of claim 1, wherein a third traction feature is disposed diametrically opposed to the first traction feature about the cross-section of the umbilicus between the first and second ends.

7. The fluid circuit of claim 1, wherein the umbilicus comprises material that includes a thermoplastic elastomer.

8. A fluid circuit for use with a fluid processing assembly, the fluid circuit comprising:
  an umbilicus having a first end, a second end, an axis of rotation, and a cross-sectional circumference;
  a one-piece bearing secured to the umbilicus at a location between the first and second ends, the bearing having an axis of rotation and including an inner lumen which directly engages the umbilicus and includes a plurality of tabs disposed about the axis of rotation of the umbilicus;
  wherein the plurality of tabs comprises:
    a first tab, disposed at a first rotational angle about the axis of rotation, having a first set of traction features disposed at a first set of lengths between the first and second ends, the first set of traction features defining all traction features disposed on the first tab, wherein the first tab is configured to engage the umbilicus at a first arrangement of compression locations between the first and second ends of the umbilicus;
    a second tab disposed at a second rotational angle about the axis of rotation, having a second set of traction features disposed at a second set of lengths between the first and second ends, the second set of traction features defining all traction features disposed on the second tab, wherein the second tab is configured to engage the umbilicus at a second arrangement of compression locations between the first and second ends of the umbilicus;
    a third tab disposed at a third rotational angle about the axis of rotation, having a third set of traction features disposed at the first set of lengths between the first and second ends, the third set of traction features defining all traction features disposed on the third tab, wherein the third tab is configured to engage the umbilicus at the first arrangement of compression locations between the first and second ends of the umbilicus; and
    a fourth tab, disposed at a fourth rotational angle about the axis of rotation, having a fourth set of traction features disposed at the second set of lengths between the first and second ends, the fourth set of traction features defining all traction features disposed on the fourth tab, wherein the fourth tab is configured to engage the umbilicus at the second arrangement of compression locations between the first and second ends of the umbilicus.

9. The fluid circuit of claim 8, wherein the traction features are oriented transversely to the axis of rotation of the bearing and umbilicus.

10. The fluid circuit of claim 8, wherein the second and fourth tabs comprise no traction features configured to engage the umbilicus.

11. The fluid circuit of claim 8, wherein each compression location within the first and/or second arrangement of compression locations of the umbilicus has a generally offset ovular cross-sectional shape when engaged by the traction features.

12. The fluid circuit of claim 8, wherein the tabs are disposed circumferentially about the axis of rotation of the bearing.

13. The fluid circuit of claim 8, wherein the first and third tabs are disposed diametrically opposed to each other about the cross-section of the umbilicus, and the second and fourth tabs are disposed diametrically opposed to each other about the cross-section of the umbilicus.

14. The fluid circuit of claim 8, wherein the umbilicus comprises material including a thermoplastic elastomer.

15. A fluid circuit for use with a fluid processing assembly, the fluid circuit comprising:
  an umbilicus having a first end, a second end, an axis of rotation, and a generally circular cross-section having a circumference;
  a one-piece bearing secured to the umbilicus at a location between the first and second ends, the bearing having an axis of rotation and including an inner lumen which directly engages the umbilicus and includes a plurality of traction features, which bear against the umbilicus at compression locations to prevent relative rotation of the bearing and the umbilicus;
  wherein the plurality of traction features comprises:
    a first traction feature which comprises a first plurality of projections disposed at a first rotational angle about the axis of rotation, the first plurality of projections defining all projections disposed on the first traction feature, and is configured to engage the umbilicus at a first arrangement of compression locations at a first set of lengths between the first and second ends of the umbilicus;
    a second traction feature which comprises a second plurality of projections disposed at a second rotational angle about the axis of rotation, the second plurality of projections defining all projections disposed on the second traction feature, and is configured to engage the umbilicus at a second arrangement of compression locations at a second set of lengths between the first and second ends of the umbilicus;
    a third traction feature which comprises a third plurality of projections disposed at a third rotational angle about the axis of rotation, the third plurality of projections defining all projections disposed on the third traction feature, and is configured to engage the umbilicus at a third arrangement of compression locations at the first set of lengths between the first and second ends of the umbilicus; and
    a fourth traction feature which comprises a fourth plurality of projections disposed at a fourth rotational angle about the axis of rotation, the third plurality of projections defining all projections disposed on the third traction feature, and is configured to engage the umbilicus at a fourth arrangement of compression locations at the second set of lengths between the first and second ends of the umbilicus;

wherein the cross-sectional shape of the umbilicus at any compression location within the first, second, third, and/or fourth arrangement of compression locations is non-circular.

16. The fluid circuit of claim 15, wherein the traction features are disposed on tabs circumferentially disposed about the axis of rotation of the bearing.

17. The fluid circuit of claim 15, wherein the first and third arrangement of compression locations are disposed diametrically opposed to each other about the cross-section of the umbilicus.

18. The fluid circuit of claim 15, wherein the first and second compression locations have an angular relationship of 90 degrees about the cross-sectional circumference.

* * * * *